United States Patent [19]

Baier

[11] Patent Number: 4,639,425

[45] Date of Patent: Jan. 27, 1987

[54] HETEROGENEOUS IMMUNOASSAY AND REAGENT THEREFORE

[75] Inventor: Manfred Baier, Pocking-Possenhofen, Fed. Rep. of Germany

[73] Assignee: Boehringer Mannheim GmbH, Mannheim, Fed. Rep. of Germany

[21] Appl. No.: 631,816

[22] Filed: Jul. 17, 1984

[30] Foreign Application Priority Data

Jul. 30, 1983 [DE] Fed. Rep. of Germany ....... 3327642

[51] Int. Cl.⁴ ................. G01N 33/543; G01N 33/544; G01N 33/545; G01N 33/546
[52] U.S. Cl. ........................................ 436/518; 435/7; 436/528; 436/529; 436/530; 436/531; 436/532; 436/533; 436/534; 436/825; 436/826
[58] Field of Search ......................... 436/518, 528–534, 436/825, 826; 435/7

[56] References Cited

U.S. PATENT DOCUMENTS

| | | | |
|---|---|---|---|
| 4,200,436 | 4/1980 | Mochida et al. | 424/1.1 |
| 4,241,175 | 12/1980 | Miller et al. | 435/7 |
| 4,267,270 | 5/1981 | Stout | 436/518 |
| 4,273,756 | 6/1981 | Ling et al. | 424/1.1 |
| 4,273,867 | 6/1981 | Lin et al. | 424/1.1 |
| 4,313,927 | 2/1982 | Fridlender | 435/7 |
| 4,492,762 | 1/1985 | Wang et al. | 436/825 |

OTHER PUBLICATIONS

Chard, from Laboratory Techniques in Biochemistry and Molecular Biology, vol. 6, part 2, Work et al., eds., Elsevier Bio Medical, Amsterdam, 1982, p. 17.

*Primary Examiner*—Christine M. Nucker
*Attorney, Agent, or Firm*—Felfe & Lynch

[57] ABSTRACT

The invention is an improvement in a heterogeneous immunoassay, and reagent therefore, for the determination of a substance in a blood serum or plasma sample, such as a parnter of an immune reaction, in which one of the reaction partners is adsorbed on a solid carrier, the improvement comprises adding a detergent to the incubation medium of the reaction, in an amount of 0.0001 to 0.01% (w/v) to reduce interferences from the serum or plasma.

7 Claims, 4 Drawing Figures

HETEROGENEOUS IMMUNOASSAY AND REAGENT THEREFORE

The present invention is concerned with a process for the determination of a partner of an immune reaction in a serum or plasma sample in which one of the reaction partners is adsorbed on a solid carrier.

It has been known for many years that immunological determinations in serum and plasma lead to different results. Inhibitory factors are deemed to be responsible for this, these factors being present in blood plasma and influencing the activity of the binding partner adsorbed on a solid carrier.

In Clin. Chem., 24, 137–139/1978, there are indicated, for example, the differences between serum and plasma samples for numerous radioimmunological determinations. That differing values for measurements in serum and plasma are also found for an enzyme immunoassay is described, for example, in Arztl. Lab., 27, 69–73/1981. In this work, the conclusion is also drawn that such component materials of plasma, especially fibrinogen, lead to disturbances of the immune reaction between the adsorbed and the soluble partner or partners in the case of all enzyme immunoassays in which the principle of a heterogenous process is employed.

However, in practice, it can, in general, not be avoided also to use plasma as sample medium. Furthermore, it is sometimes not known at all, in the case of a sample to be measured, whether it has been prepared on the basis of a serum or of a plasma.

Thus, there is a need for a process for the determination of a partner of an immune reaction in which one partner is present in a form adsorbed on a solid carrier which, independently of the sample material, i.e. serum or plasma, gives dependable and agreeing values. In Artzl. Lab., 27, 69–73/1981, it is suggested to heat the sample for 10 minutes at 56° C. in order to overcome the mentioned disturbances and subsequently to centrifuge off the denatured disturbing substances. However, this heating step with subsequent centrifuging means, in the practical carrying out of the determination process, additional working steps. Furthermore, it is thereby to be reckoned that other kinds of disturbances and sources of error are brought about by the heat treatment.

Therefore, it is an object of the present invention to provide a process which gives comparable values not only in serum but also in plasma samples and, in addition, can be carried out in a simple manner and without additional process steps.

This object of achieved by adding a detergent to the incubation medium of the immune reaction between the soluble partner or partners and the binding partner adsorbed on a solid carrier.

Thus, according to the present invention, there is provided a process for the determination of a partner of an immune reaction in a serum or plasma sample in which one of the reaction partners is adsorbed on a solid carrier, wherein a detergent is added to the incubation medium of the immune reaction between the soluble partner or partners and the binding partner adsorbed on a solid carrier.

The present invention also provides a reagent for carrying out an immune reaction between a reaction partner adsorbed on a solid phase and a soluble partner or partners in a serum or plasma sample, wherein, in addition to the components necessary for the immune reaction, it also contains a detergent.

The detergent concentration in the reagent is preferably from 0.0001 to 0.01% w/v and especially preferably from 0.001 to 0.005% w/v.

The reagent according to the present invention can be in the form of a powder, lyophilisate or solution.

The detergents used can be non-ionic or anionic. Examples of non-ionic detergents include epoxy-fatty acid esters, for example Tween 20 (polyoxyethylene-sorbitan monolaurate), Tween 80 (polyoxyethylene-sorbitan monooleate), Triton (alkyl-polyether-alcohol mixtures), Brij 35 (polyoxyethylene lauryl ether), Nonidet P-40 (polyoxyethylene octylphenol ether), Lubrol PX (polyethylene oxide-alkyl ether adduct), Berol EMU 043 (C16,C18 fatty alcohol with 10 oxyethylene units) and the like. As an example of an anionic detergent, there is to be mentioned sodium dodecyl sulphate (SDS).

The detergents are preferably added to the incubation solution in a concentration of from 0.0001 to 0.01% w/v and especially preferably of from 0.001 to 0.005% w/v.

It was known to suppress or remove non-specific bindings in an immune reaction by the addition of detergents. If, in the case of an immune reaction, one binding partner is used in a form adsorbed on a solid carrier, then hitherto an addition of detergents was avoided since the adsorptive binding of the binding partner to the carrier is weakened or completely removed.

It is surprising that the addition, according to the present invention, of detergents in the said low concentrations completely excludes the inhibitory factors of the blood plasma without impairing the adsorptive binding of the binding partner to the solid carrier.

By an immune reaction within the meaning of the present invention, there are to be understood all reactions between immunological receptors and acceptors. The only thing which is important according to the present invention is that one reaction partner in the reaction or also only in a partial step of the whole reaction is used in a form adsorbed on a solid carrier.

As an example of the numerous known variants of such immunological determination processes, there may be mentioned the competitive assay in which, for the determination of an acceptor in a sample, a known amount of the tagged acceptor is added to a sample and the acceptor and the tagged acceptor compete for receptor binding positions which are present in insufficient amount, the binding positions being on a solid carrier. A further wide field are the sandwich tests in which an at least bivalent acceptor is reacted with a tagged receptor and a receptor adsorbed on a solid carrier. This reaction can take place in various ways:

(a) The acceptor is reacted simultaneously with the tagged and the insoluble receptor.

(b) In the first step, there takes place the reaction between acceptor and the insoluble receptor. The resultant complex is incubated in a second step with the tagged receptor.

(c) In the first step, there takes place the reaction between the acceptor and the tagged receptor. The resultant soluble complex is subsequently reacted with the insoluble receptor.

The addition of the detergent according to the present invention takes place, in each case, in the step in which the receptor adsorbed on a solid phase participates in the reaction.

By an acceptor, there is, in particular, to be understood an antigen or hapten. As receptors, there can be used complete antibodies or also antibody fragments. Tagging can take place in known manner by an enzyme, a radioisotope, a fluorescing compound or the like.

As solid phase, there can be used platelets, spheroids, tubes, strips or rodlets of glass, synthetic resins or similar materials.

Figure 1:
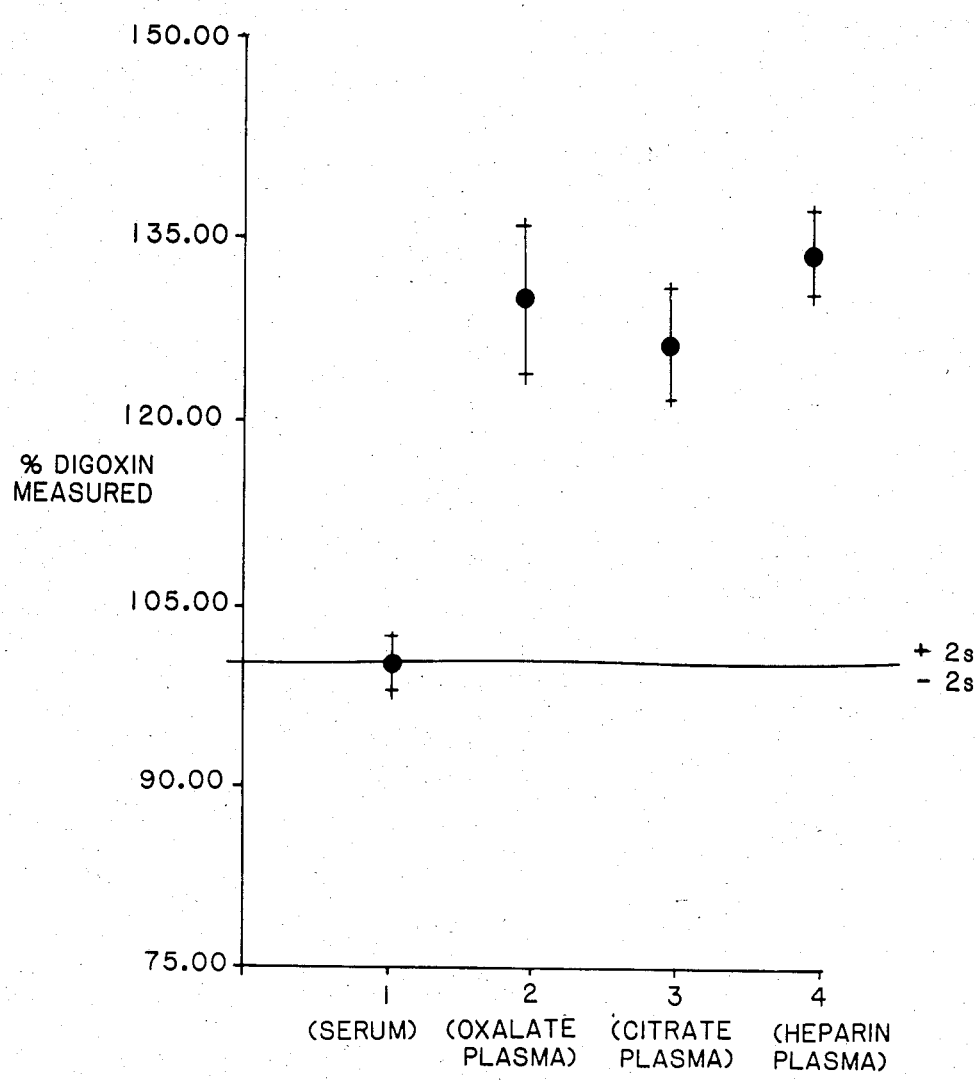
FIG. 1 shows the percent digoxin measured in various sample media without the addition of detergent.

The following Examples are given for the purpose of illustrating the present invention:

EXAMPLE 1

Determination of digoxin with the help of a competitive ELISA test

Sheep anti-digoxin is, depending upon the titre, diluted in appropriate manner with phosphate buffer (10 mM; pH 7.5), placed into reagent tubelets made of polystyrene and incubated overnight. Furthermore, into the tubelets are pipetted 1000 μl. conjugate buffer, digoxin peroxidase (20 mU/ml.) in phosphate buffer (40 mM; pH 6.8), bovine serum albumin 0.25%, as well as in one case once no detergent and in one case 0.003% Tween 20, and also 100 μl. digoxin-containing serum or plasma. The mixture is incubated for 1 hour at ambient temperature. Thereafter, the tubelets are sucked out and washed with tap water.

The covalent binding (coupling) of peroxidase on to antibody takes place according to the method of Wilson and Nakane, described in "Recent developments in the periodate method of conjugating horse radish peroxidase (HRPO) to antibodies", 1978, pages 215–224, pub. Elsevier/North-Holland Biomedical Press, in "Immune fluorescence and related staining techniques".

Subsequently, the peroxidase activity on the surface of the polystyrene tubelets is determined in known manner. For this purpose, 1000 μl. substrate solution which contains 2,2'-azino-di-(3-ethylbenzthiazoline-6-sulphonate) (ABTS) and hydrogen peroxide in 100 mM phosphate/citrate buffer (pH 4.4) are pipetted into the tubelets and incubated for 1 hour at ambient temperature. Subsequently, the extinctions are measured in a photometer. By the measurement of standard samples with a known digoxin concentration, there is prepared a calibration curve. From the extinction of the samples with unknown digoxin concentration, with the help of this calibration curve there is determined the digoxin concentration in the unknown sample.

In FIG. 1 of the accompanying drawings, there is illustrated the percentage digoxin value found in various sample media when the above-described test is carried out in the absence of a detergent. 1 shows the 100% value for clear human serum which contains 1.0 ng./ml. digoxin. The corresponding values for various plasma samples (2=oxalate plasma, 3=citrate plasma and 4=heparin plasma) are also shown in FIG. 1. The values clearly show that, in the absence of a detergent, a substantially increased digoxin concentration is simulated.

Figure 2:
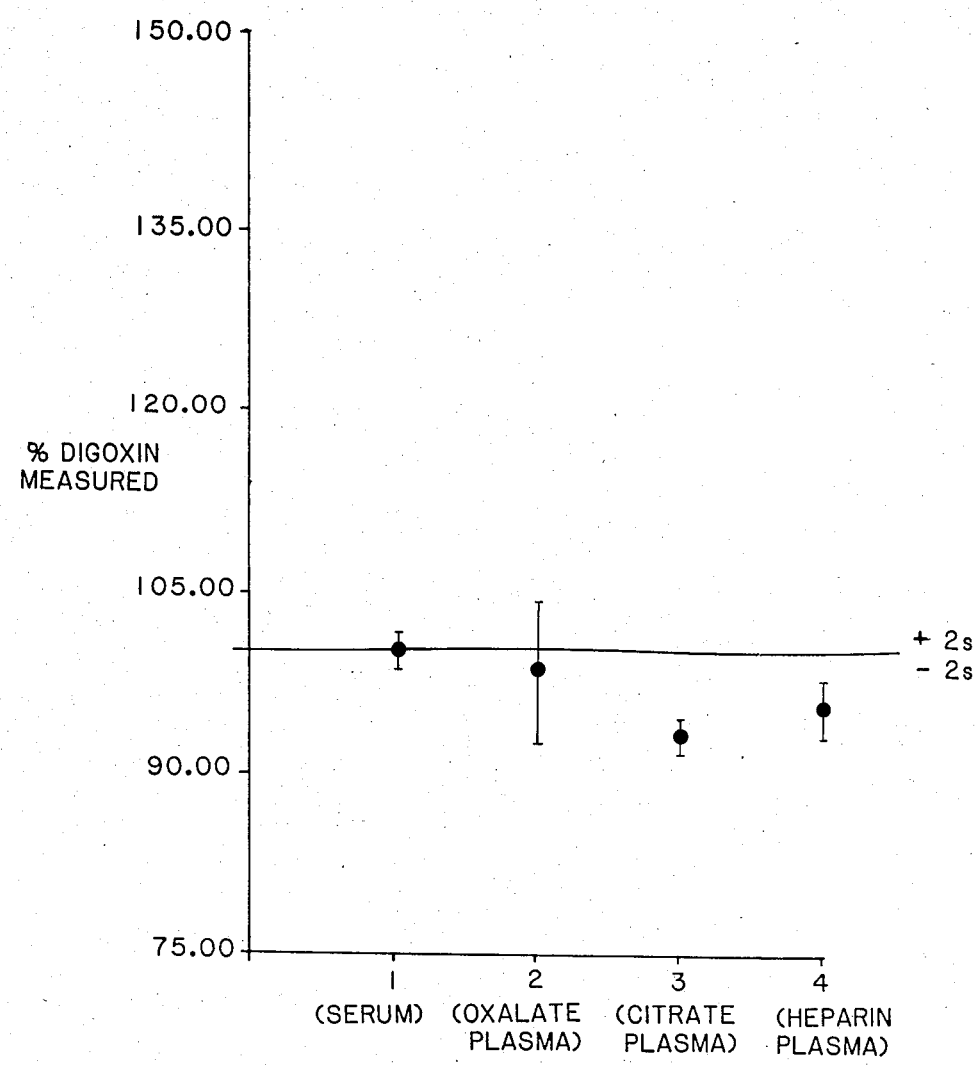
FIG. 2 is similar to FIG. 1 but measurements were made with the addition of 0.003% Tween 20.

In FIG. 2 of the accompanying drawings, there are given the corresponding values for measurements which have been carried out in a fully analogous manner but with the addition of 0.003% Tween 20, as stated above. The values given in FIG. 2 show that, in the latter case, only slight deviations are to be observed.

EXAMPLE 2

Determination of AFP (alpha-1-foetoprotein) with the help of a sandwich ELISA test In the manner described in Example 1, synthetic resin tubelets are adsorptively coated with sheep anti-AFP. The tubelets are dried and subsequently used as follows:

1000 μl. of an incubation buffer, which consists of 100 mM phosphate buffer (pH 6.8) in 1% bovine serum albumin, and 200 μl. of sample or standard are introduced into the tubelets and incubated for 1 hour at ambient temperature. Subsequently, they are sucked out, washed once with tap water and a conjugate solution consisting of sheep anti-AFP, to which peroxidase is coupled, is added thereto. The mixture is incubated for 1 hour at ambient temperature. Subsequently, they are again sucked out, washed with tap water and incubated with 1000 μl. substrate solution which consists of ABTS/hydrogen peroxide in 100 mM phosphate-citrate buffer (pH 4.4.). A calibration curve is prepared with the help of standard samples with known AFP content. On the basis of these calibration curves, there are determined the AFP concentrations in the unknown samples.

Figure 3:
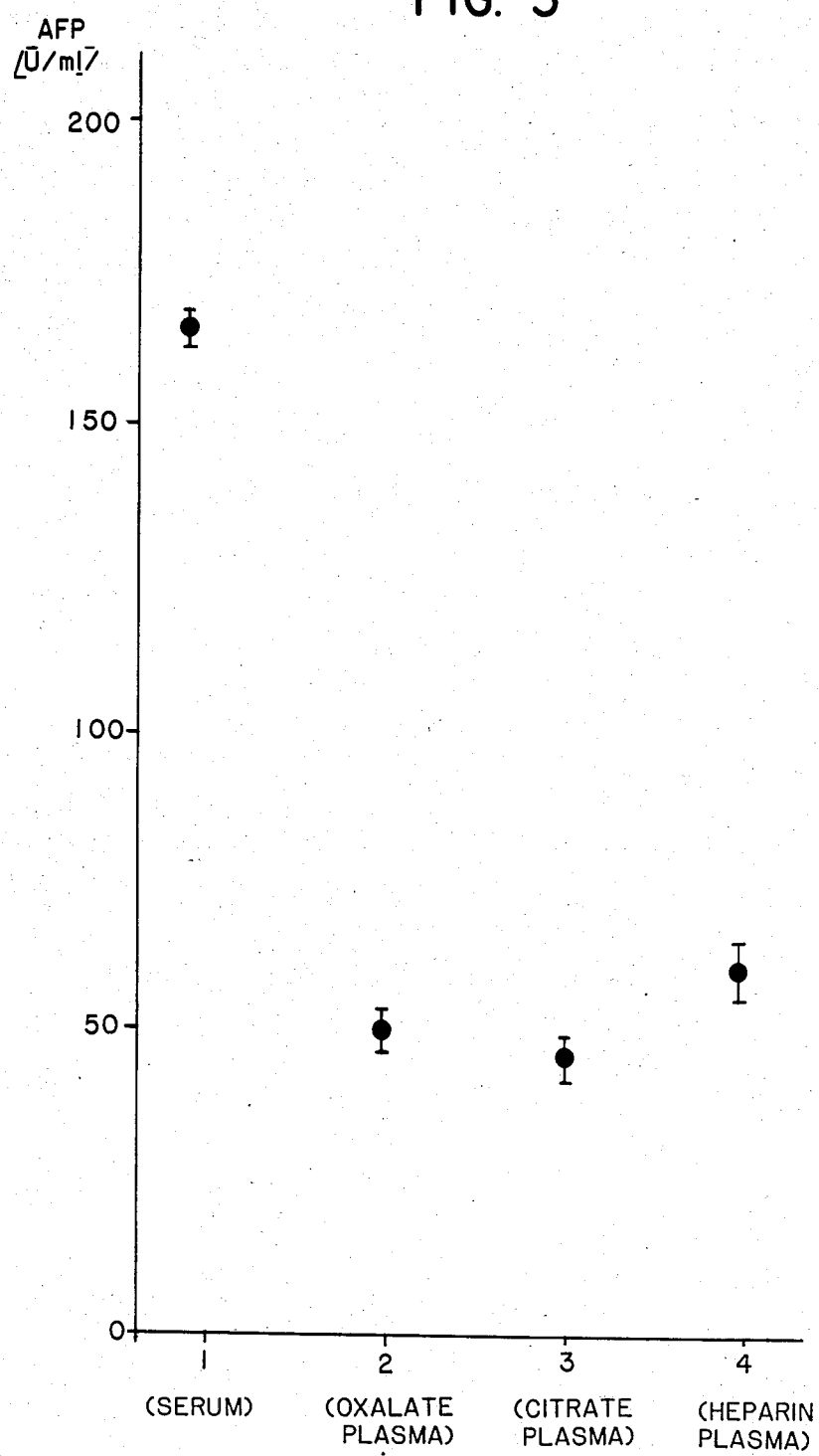
FIG. 3 shows the concentration of AFP (alpha-1-foetoprotein) measured in various sample media without the addition of detergent.

In FIG. 3 of the accompanying drawings, there are shown the AFP values found according to the above process for serum, oxalate plasma, citrate plasma and heparin plasma, without the addition of a detergent according to the present invention. The values found show that drastically smaller AFP concentrations are measured in the plasma samples.

Figure 4:
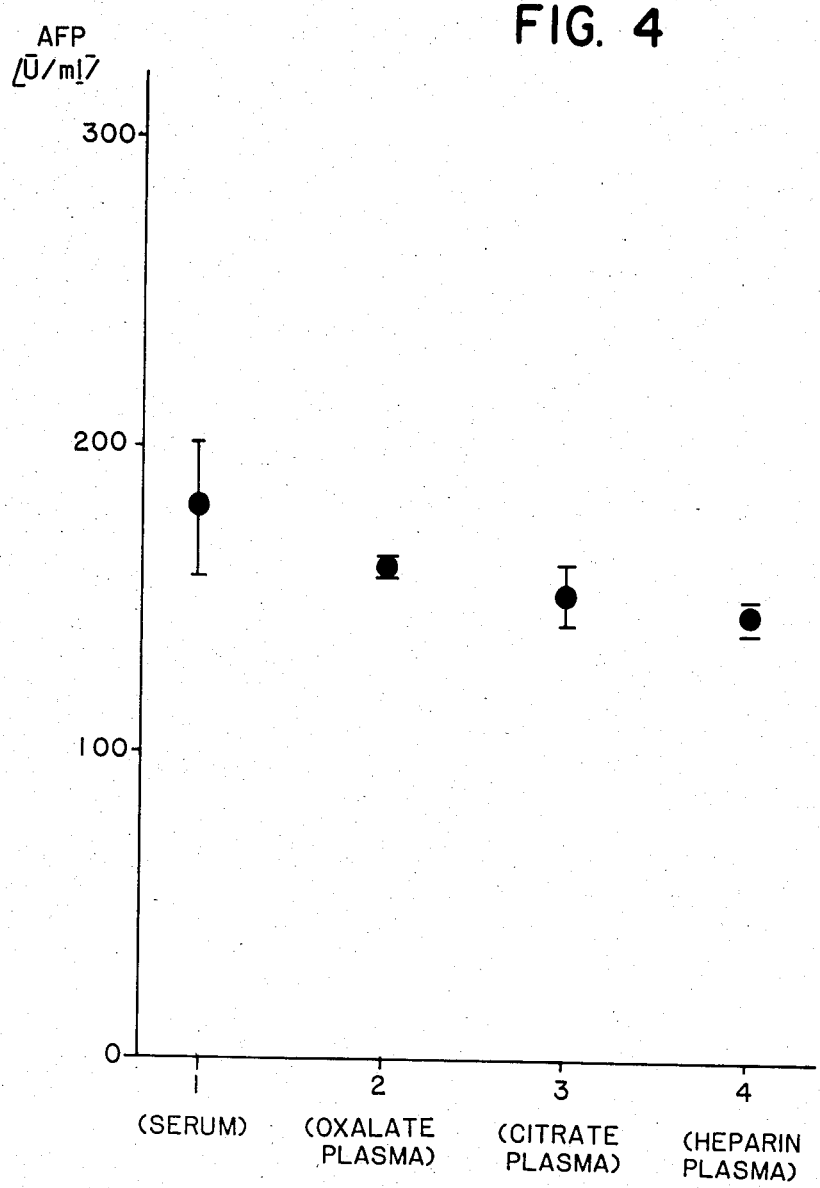
FIG. 4 is similar to FIG. 3 but measurements were made with the addition of 0.002% Tween 20.

In FIG. 4 of the accompanying drawings, there are shown the corresponding values obtained when, in the manner according to the present invention, 0.002% Tween 20 is added in the case of the incubation. The deviations between serum and plasma are small. In general, they lie within the limits of error.

Completely analogous results are obtained when, in the case of the above-described determination process, instead of 0.002% Tween, there is used 0.003% Brij 35 as detergent.

EXAMPLE 3

Determination of thyrotropin (TSH) with the help of a sandwich ELISA test

In the manner described in Examples 1 and 2, synthetic resin tubelets are adsorptively coated with monoclonal antibodies from mice, directed against TSH, and, after drying, used as follows:

1000 μl. incubation solution, which contains 100 mM phosphate buffer (pH 6.8) and 1% bovine serum albumin, are, together with 200 μl. sample solution from serum or plasma which contain differing amounts of TSH, incubated for 1 hour at ambient temperature. After subsequently sucking out and washing, incubation is carried out with 1000 μl. conjugate solution containing sheep anti-TSH to which peroxidase is coupled. The incubation time is 1 hour at ambient temperature. After subsequent sucking out and washing, further processing is carried out in the manner described in Examples 1 and 2.

This determination process is carried out once without the addition of a detergent and also once with the addition of 0.005% Tween 20. The values found for serum, as well as for various plasma samples, are compared in the following Table.

TABLE

Determination of TSH in serum and various plasma samples without the addition of a detergent and with the addition of 0.005% Tween 20

|  | without addition of detergent | with 0.005% Tween 20 |
|---|---|---|
| serum | 13.0 $\mu$U/ml. | 12.0 $\mu$U/ml. |
| oxalate plasma | 8.1 $\mu$U/ml. | 11.2 $\mu$U/ml. |
| citrate plasma | 9.7 $\mu$U/ml. | 11.1 $\mu$U/ml. |
| heparin plasma | 8.6 $\mu$U/ml. | 10.6 $\mu$U/ml. |

In this case, too, it can be clearly seen that, without the addition of a detergent, the values for serum and plasma samples clearly differ from one another. In the case of the addition according to the present invention of a detergent, the measured values for serum and plasma agree well with one another.

It will be understood that the specification and examples are illustrative but not limitative of the present invention and that other embodiments within the spirit and scope of the invention will suggest themselves to those skilled in the art.

What is claimed is:

1. In a heterogeneous immunoassay for the determination of a partner of an immune reaction in a blood serum or plasma sample in which one of the reaction partners is adsorbed on a solid carrier, the improvement comprising adding a detergent in such an amount to the incubation medium of the immune reaction between the soluble partner or partners and the partner adsorbed on the solid carrier that its concentration is from 0.0001 to 0.01% (w/v).

2. The immunoassay of claim 1 wherein the detergent is a non-ionic or anionic detergent.

3. The immunoassay of claim 1, wherein the detergent used is a polyoxyethylenesorbitan monolaureate, a polyoxyethylene-sorbitan monooleate, an alkyl-polyether-alcohol mixture, a polyoxyethylene lauryl ether, polyoxyethylene octylphenol ether, a polyethyleneoxide-alkyl ether adduct, a C16 or C18 fatty alcohol with 10 oxyethylene units or sodium dodecyl sulphate.

4. In a competitive heterogeneous immunoassay for the determination of a substance in a blood serum or plasma sample of the type in which a known amount of a tagged substance is added to the sample solution whereupon the substance to be determined and the tagged substance compete for the binding points of a receptor present in insufficient amount, the receptor being adsorbed on a solid carrier, the improvement comprising adding, a detergent in such an amount to the incubation medium of the immune reaction that its concentration is 0.0001 to 0.01% (w/v).

5. In a heterogeneous sandwich immunoassay for the determination of a bivalent or multivalent substance in a blood serum or plasma sample, of the type in which the substance is brought into contact with a tagged receptor and with a receptor adsorbed on a solid carrier, the improvement comprising adding a detergent in such an amount to the incubation medium of the immune reaction between the acceptor and the receptor adsorbed on a solid carrier that its concentration is 0.0001 to 0.01% (w/v).

6. In a reagent for carrying out an immune reaction between a reaction partner adsorbed on a solid carrier and a soluble partner or partners in a blood serum or plasma sample the improvement comprising a detergent in such an amount that it is present in a concentration of 0.0001 to 0.01% (w/v).

7. The reagent of a claim 6, wherein the detergent is a non-ionic or anionic detergent.

* * * * *